US00PP24644P3

(12) United States Plant Patent
Schäfer

(10) Patent No.: US PP24,644 P3
(45) Date of Patent: Jul. 15, 2014

(54) VARIETY OF BASIL PLANT NAMED 'DARK LADY'

(50) Latin Name: *Ocimum basilicum*
Varietal Denomination: Dark Lady

(75) Inventor: Udo Schäfer, Wolsier (DE)

(73) Assignee: Herbalea GmbH, Grolsheim (DE)

( * ) Notice: Subject to any disclaimer, the term of this patent is extended or adjusted under 35 U.S.C. 154(b) by 119 days.

(21) Appl. No.: 13/385,798

(22) Filed: Mar. 7, 2012

(65) Prior Publication Data

US 2013/0239270 P1 Sep. 12, 2013

(51) Int. Cl.
*A01H 5/00* (2006.01)

(52) U.S. Cl.
USPC ..... Plt./258

(58) Field of Classification Search
USPC ..... Plt./258
See application file for complete search history.

(56) References Cited

U.S. PATENT DOCUMENTS

PP13,486 P2 * 1/2003 Bowden et al. ..... Plt./258
PP16,260 P2 * 2/2006 Bennerup ..... Plt./258

OTHER PUBLICATIONS

PLUTO UPOV database QZ citation for 'Dark Lady' Feb. 15, 2011.*

* cited by examiner

*Primary Examiner* — Wendy C Haas
(74) *Attorney, Agent, or Firm* — The Webb Law Firm

(57) ABSTRACT

'Dark Lady' is a new variety of basil plant having tolerance to low temperatures, a sweet-spicy taste, and dark violet leaves with prominent veins.

7 Drawing Sheets

Botanical classification: *Ocimum basilicum.*
Varietal denomination: 'DARK LADY'.

BACKGROUND OF THE NEW PLANT

The present invention comprises a new and distinct cultivar of basil plant, botanically known as *Ocimum basilicum* and hereinafter referred to by the cultivar name 'Dark Lady'.

The new variety was discovered and selected by the breeder in a cultivated environment in July of 2009 in Wolsier, Germany (located in the region of Brandenburg) as a naturally occurring open-pollinated new variety in a population of unpatented and unnamed *Ocimum basilicum* plants. Subsequently, the new variety was asexually reproduced by cuttings in Wolsier, Germany in 2010. Further asexual reproductions at the same location has demonstrated that the combination of characteristics as herein disclosed for the new cultivar are retained and reproduced true to type through successive generations of asexual reproduction.

The following observations, measurements and comparisons describe 8-week-old plants grown in an open field with full sun, watered as needed, and receiving weekly fertilization treatments accented with nitrogen in Wolsier, Germany. The plants were exposed to daytime temperatures of 20-30° C., and evening temperatures of 10-20° C. Color observations were taken under natural light, and the color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Dark Lady' which, in combination, distinguish this basil plant as a new and distinct cultivar:

1. Tall and well-branched plant habit;
2. Sweet-spicy fragrance;
3. Aromatic taste;
4. Tolerant to Fusarium, Botrytis, and Pythium; and
5. Low temperature tolerance.

Further, the new variety exhibits a tall and well-branched habit like basil variety 'Ajaka' (U.S. Plant patent application Ser. No. 13/385,808). However, 'Dark Lady' has very dark violet leaves and an aromatic fragrance, while 'Ajaka' has green leaves and a sweet-spicy fragrance. The following Table 1 provides a further comparative listing of botanical characteristics of 'Dark Lady' and 'Ajaka'.

TABLE 1

| Botanical characteristics | 'Dark Lady' | 'Ajaka' |
|---|---|---|
| Height from soil to top of plant: | 50 cm. | 60 cm. |
| Leaf length: | 4.5 cm. | 5 cm. |
| Number of flowers per plant: | About 200 | About 150 |
| Flower longevity: | 6-8 weeks | 4-6 weeks |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
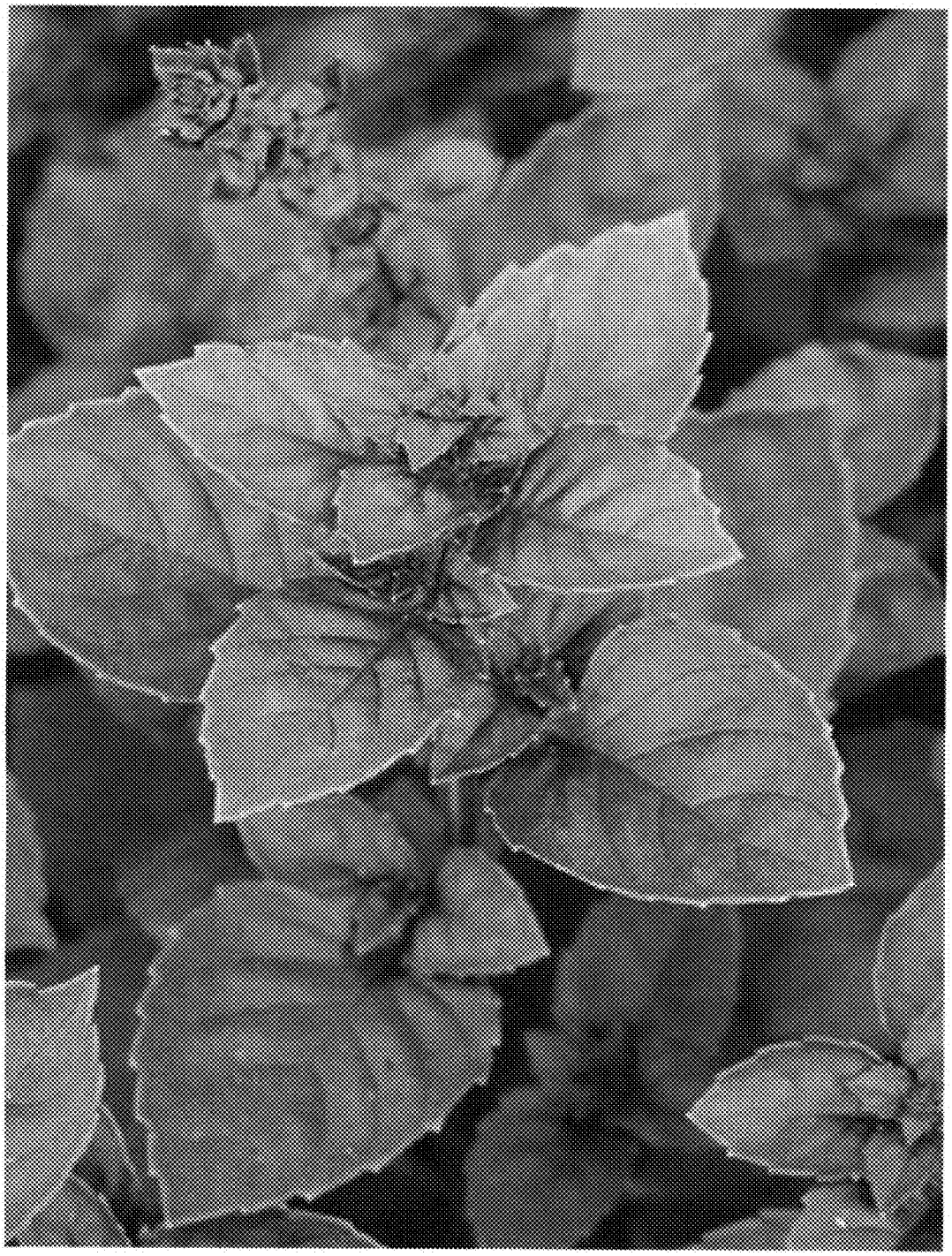
FIG. 1 is a close-up photograph of the leaves of the new variety.
Figure 2:
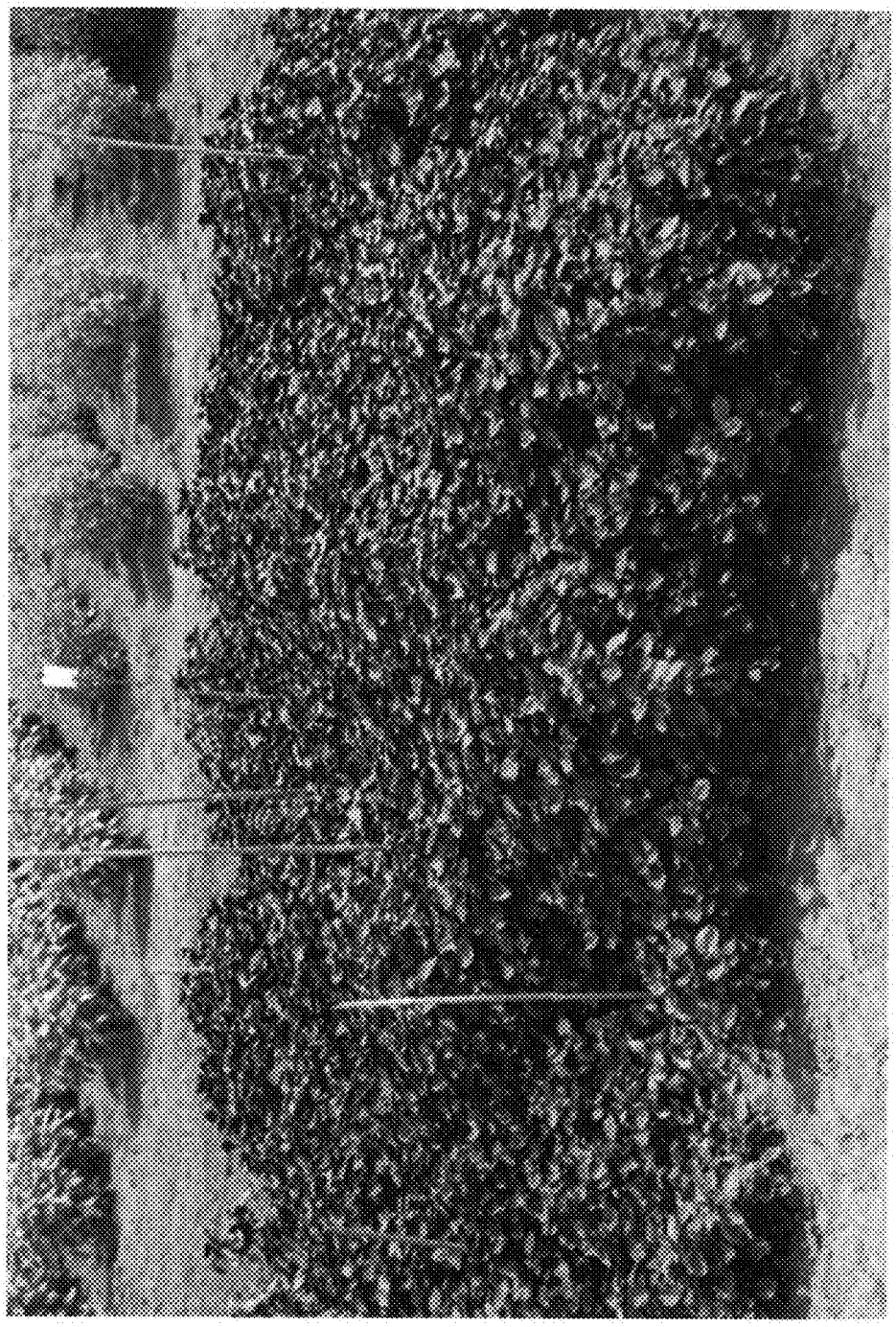
FIG. 2 is a photograph of a field of plants of the new variety.
Figure 3:
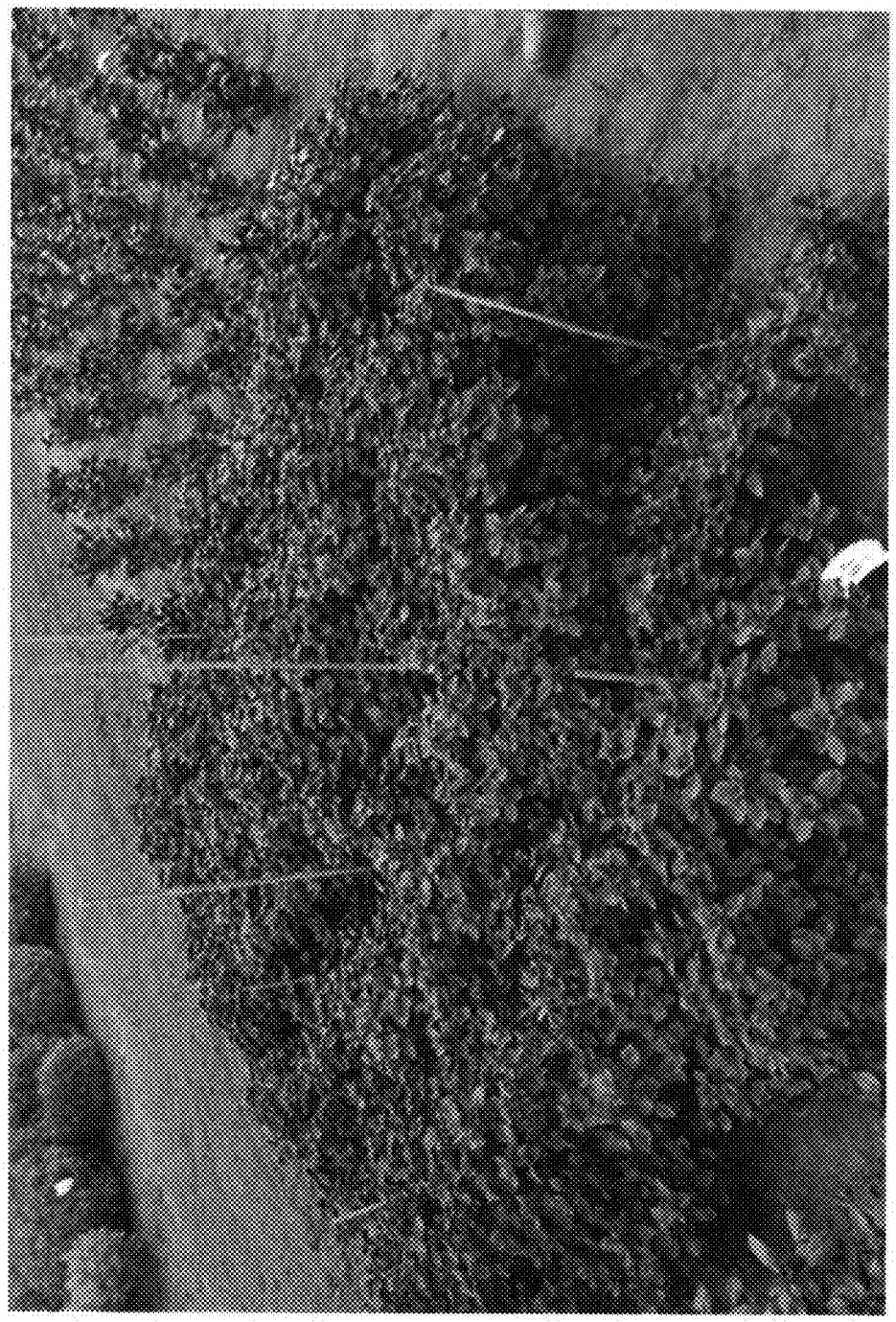
FIG. 3 is a another photograph of a field of plants of the new variety.
Figure 4:
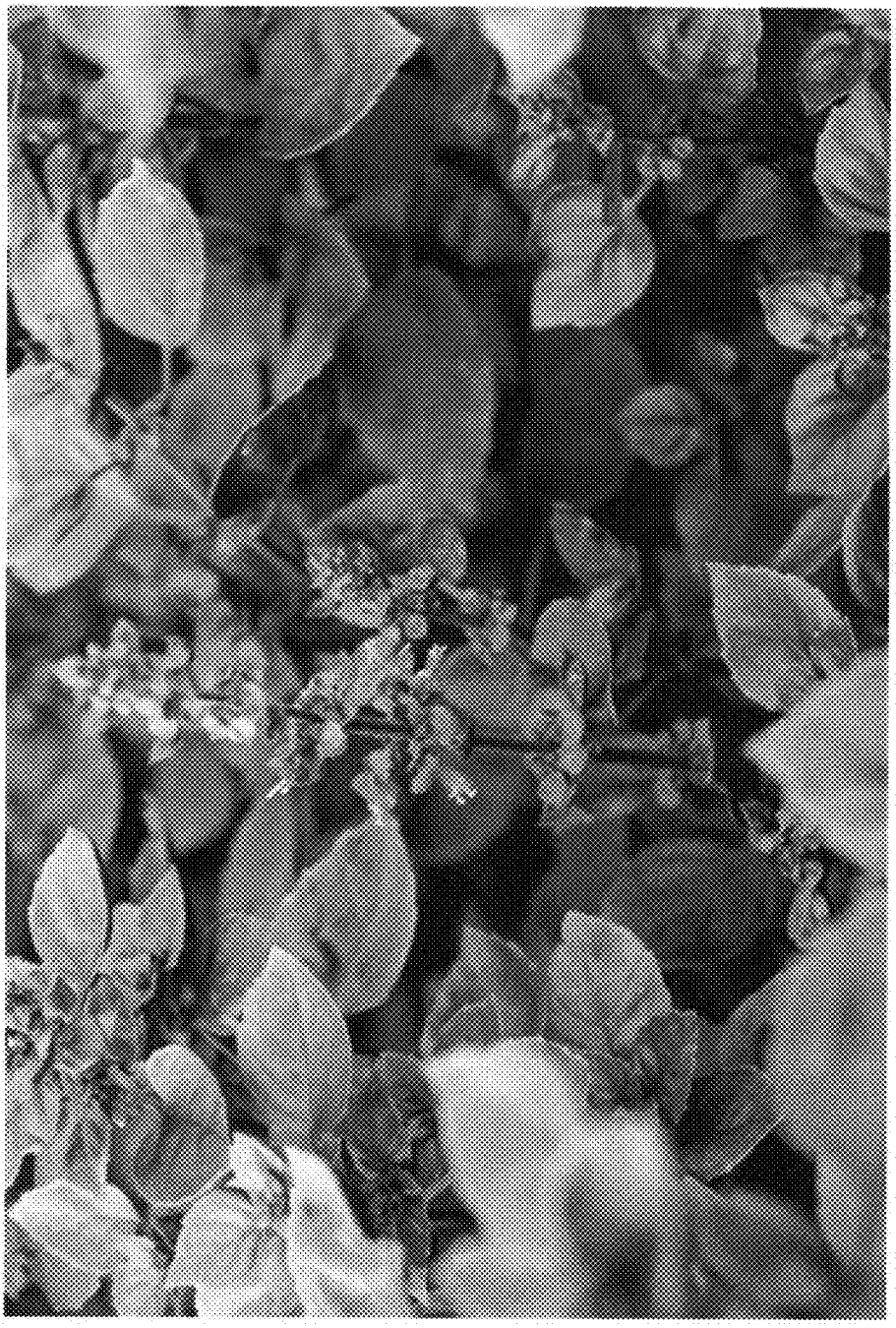
FIG. 4 is a close-up photograph of the flowers of the new variety.
Figure 5:
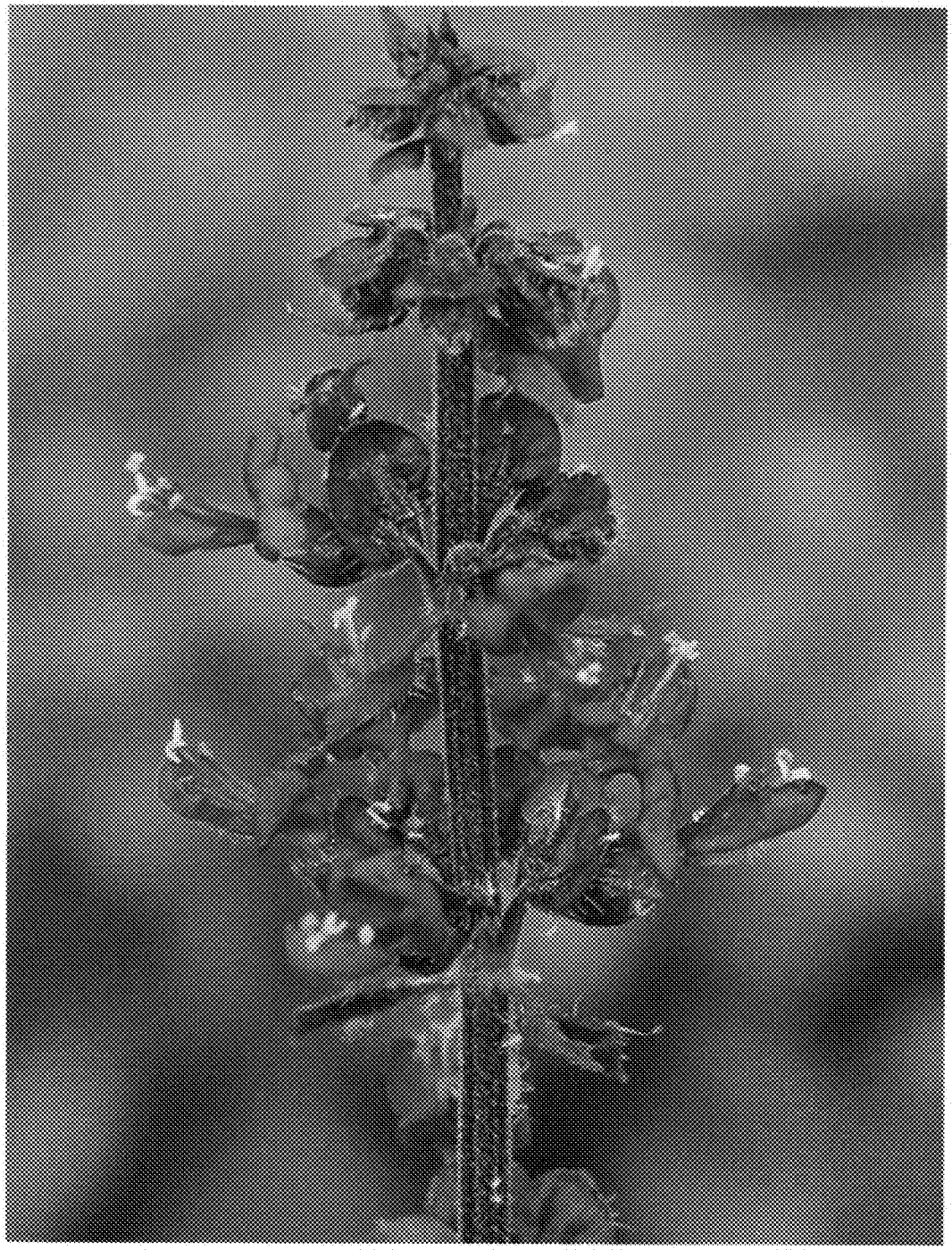
FIG. 5 is another close-up photograph of the flowers of the new variety.
Figure 6:
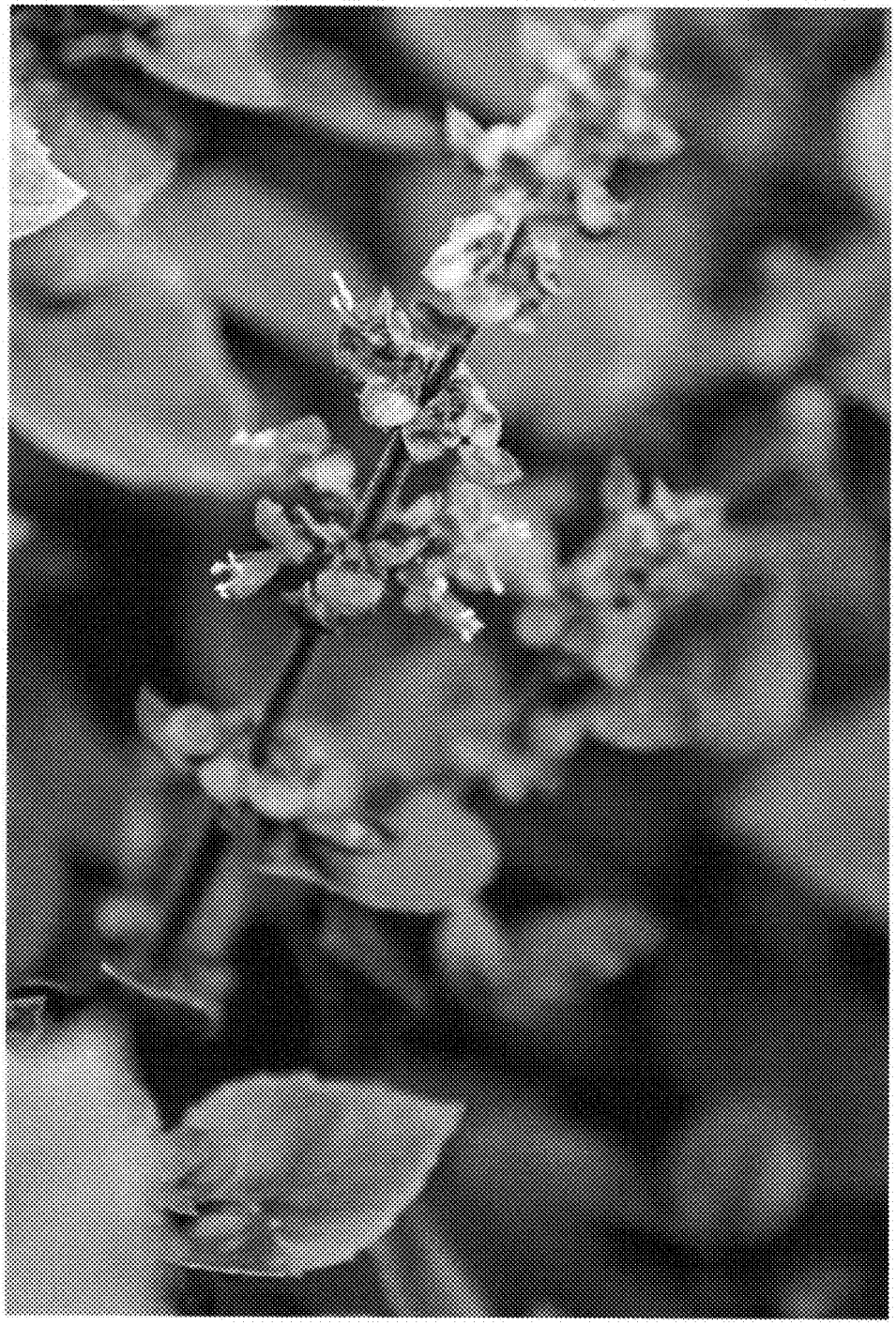
FIG. 6 is a further close-up photograph of the flowers of the new variety.
Figure 7:
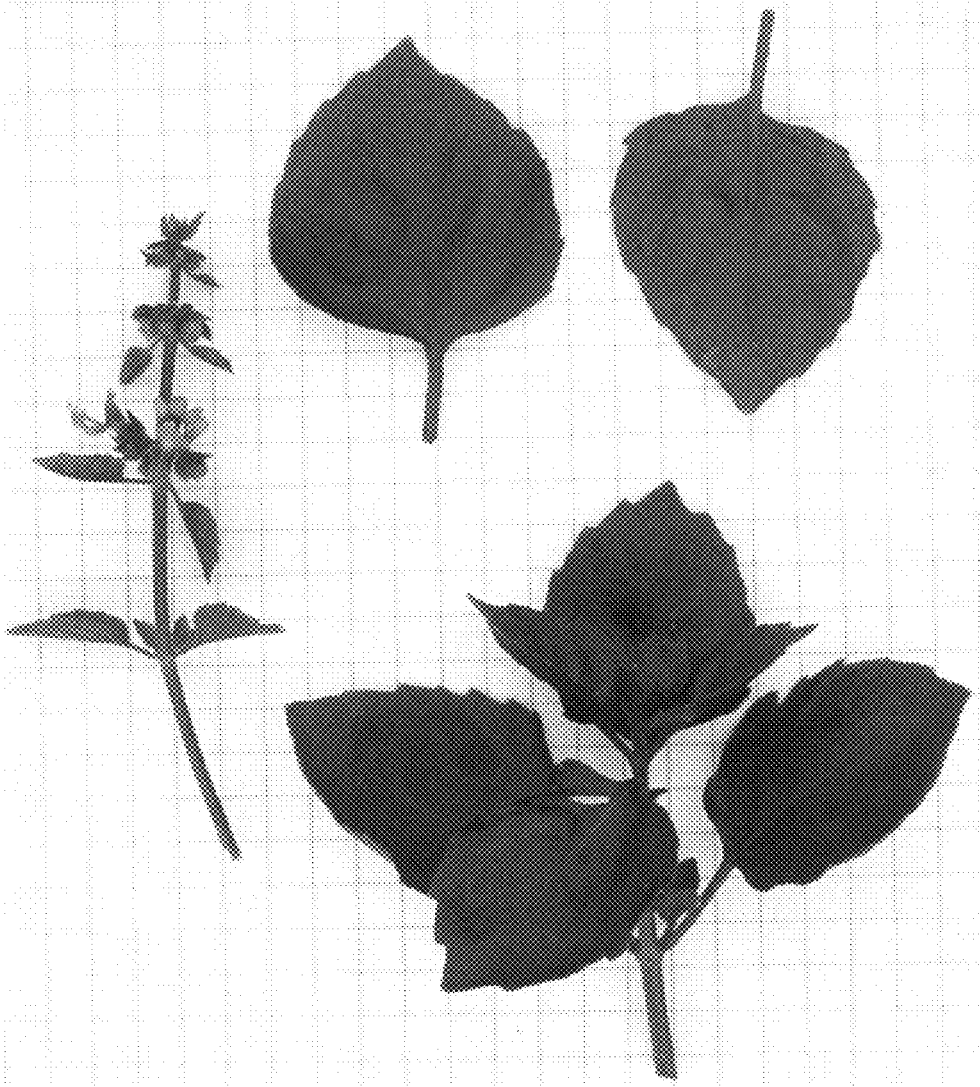
FIG. 7 is a photograph of detached leaves and flowers of the new variety.

Time to initiate roots: 5 days at 22° C.
Time to produce a rooted plant: 9 days at 22° C.
Root description: Finely branched white roots with a fibrous habit.
Form: Erect.
Height from soil to top of plant: 50 cm.
Plant diameter: 40 cm.
Growth habit: Erect and loose with a low-branching habit.
*Vigor*.—Very strong, when compared to 'Wild Magic' (U.S. Plant patent application Ser. No. 13/385,805) and 'Green Ball' (U.S. Plant patent application Ser. No. 13/385,809).
Main stem:
*Length*.—50 cm.
*Width*.—0.5 cm.
*Color*.—Purple Group RHS N77B to Violet Group RHS 83A.
*Number of branches*.—5-7.
*Node spacing*.—3-5 cm.
Leaves:
*Arrangement*.—Decussate; pinnate.
*Number of leaves per plant*.—About 400.
*Length*.—4.5 cm.
*Width*.—3.5 cm.
*Shape of leaf* (*generally*).—Broadly ovate.
*Shape of apex*.—Acute.
*Shape of base*.—Broadly ovate.
*Texture*.—Very soft and plain on the upper surface of the leaf. The veins are very strong and visible, especially on the lower leaf surface.
*Aspect*.—Horizontal.
*Margin type*.—Moderate serration present.
*Upper surface color*.—Violet Group RHS 83A up to a blackish-violet color.
*Lower surface color*.—Violet Group RHS 83A up to a blackish-violet color.
*Veins*.—Upper surface description and color: Pinnate; Violet Group RHS 83A up to a blackish-violet color. Lower surface description and color: Pinnate; Violet Group RHS 83A up to a blackish-violet color.
*Petiole*.—Length: 2 cm. Diameter: 2 mm. Color: Violet Group RHS 83A up to a blackish-violet color. Texture: Hairy. Shape: Round.
Reproductive organs: 1 pistil and 4 stamens present.
Flowers:
*Natural flowering season*.—July through September in the Brandenburg Region of Germany.
*Number of flowers per plant*.—About 200.
*Fragrance*.—Aromatic.
*Longevity*.—6-8 weeks.
*Flower type*.—Labiate.
*Flower height*.—0.5 cm.
*Flower diameter*.—0.3 cm.
*Petal color*.—Upper surface: Red-Purple Group RHS N74A. Lower surface: Red-Purple Group RHS N74A.
Seed description: Sterile.
Disease/pest resistance: Resistant to *Botrytis cinerea* and tolerant to *Fusarium oxysporum*.
Weather tolerance: Very tolerant to rain and cold nights (down to 8° C.).
Harvesting season: Early summer to fall outdoors; year round indoors.
Flavor: Sweet-spicy.
Aroma: Condimental.
Essential oils: Linalool-type.
Productivity/yield per acre:
*Fresh*.—8 tons per acre.
*Dried*.—1 tons per acre.
Average life span: 5 months.
Use: Multiple uses. The new variety can be used as a pot plant, ornamental plant, culinary herb, or fresh and dried herb.
Fresh shelf life: Over 1 week under cool conditions (5-8° C.).

I claim:

1. A new and distinct variety of basil plant named 'Dark Lady' as herein described and illustrated.

* * * * *

UNITED STATES PATENT AND TRADEMARK OFFICE

CERTIFICATE OF CORRECTION

PATENT NO. : PP24,644 P3
APPLICATION NO. : 13/385798
DATED : July 15, 2014
INVENTOR(S) : Udo Schäfer It is certified that error appears in the above-identified patent and that said Letters Patent is hereby corrected as shown below:

Title page, Column 1, Line 1, above "Botanical classification:"
insert -- CROSS REFERENCE TO RELATED APPLICATIONS
The new variety was discovered in the same cultivated area as basil plants named 'Ajaka', 'Green Ball', 'Green Fortune', 'Habana', and 'Wild Magic', each respectively claimed in U.S. Plant Patent Application Nos. 13/385,808, 13/385,809, 13/385,811, 13/385,806, and 13/385,805. --

In the Specification,
Column 4, Line 35, delete "Productivity/yield" and insert -- Productivity/Yield --

Signed and Sealed this
Eleventh Day of November, 2014

Michelle K. Lee

Michelle K. Lee
*Deputy Director of the United States Patent and Trademark Office*